(12) United States Patent
Pacetti

(10) Patent No.: US 7,850,643 B1
(45) Date of Patent: Dec. 14, 2010

(54) DRUG DIFFUSION BARRIERS FOR A CATHETER ASSEMBLY

(75) Inventor: Stephen D. Pacetti, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1332 days.

(21) Appl. No.: 09/406,473

(22) Filed: Sep. 27, 1999

(51) Int. Cl.
*A61M 29/00* (2006.01)

(52) U.S. Cl. .................................... 604/96.01

(58) Field of Classification Search ................. 428/357, 428/368, 36.92, 35.2; 623/1.1, 1.11, 1.12, 623/1.42–1.46; 604/264, 265, 266, 523, 604/530, 531; 206/210, 273, 569, 571, 363–365, 206/438, 514, 828, 484, 484.2, 524.1, 524.2; 427/2.25, 230, 2.1, 2.21, 2.3

See application file for complete search history.

(56) References Cited

U.S. PATENT DOCUMENTS

| | | | | |
|---|---|---|---|---|
| 4,254,774 A | 3/1981 | Boretos | ...................... | 128/348 |
| 4,585,452 A * | 4/1986 | Sablotsky | | |
| 4,721,204 A * | 1/1988 | Shee | | |
| 4,901,707 A * | 2/1990 | Schiff | .................... | 604/170.01 |
| 4,983,432 A | 1/1991 | Bissot | ........................ | 428/35.7 |
| 5,017,325 A | 5/1991 | Jackowski et al. | .......... | 264/521 |
| 5,049,624 A | 9/1991 | Adams et al. | ................ | 525/371 |
| 5,084,352 A | 1/1992 | Percec et al. | ................ | 428/412 |
| 5,158,548 A * | 10/1992 | Lau et al. | ..................... | 606/194 |
| 5,232,754 A | 8/1993 | Waugh | ........................ | 428/367 |
| 5,242,399 A * | 9/1993 | Lau et al. | .................... | 604/104 |
| 5,306,246 A * | 4/1994 | Sahatjian et al. | | |
| 5,352,236 A * | 10/1994 | Jung et al. | ................... | 604/103 |
| 5,417,707 A * | 5/1995 | Parkola | | |
| 5,425,710 A * | 6/1995 | Khair et al. | ............. | 604/103.05 |
| 5,565,523 A | 10/1996 | Chen et al. | .................. | 525/176 |
| 5,662,703 A * | 9/1997 | Yurek et al. | ................. | 623/1.12 |
| 5,674,192 A * | 10/1997 | Sahatjian et al. | .............. | 604/28 |
| 5,700,269 A * | 12/1997 | Pinchuk et al. | ............. | 606/108 |
| 5,700,286 A * | 12/1997 | Tartaglia et al. | | |
| 5,830,547 A * | 11/1998 | MacKenzie et al. | ......... | 206/363 |
| 5,873,880 A | 2/1999 | Williams et al. | ............ | 606/108 |
| 5,885,699 A | 3/1999 | Watson et al. | ................ | 428/212 |

OTHER PUBLICATIONS

W.E. Wailes; "Improvement in Barrier Properties of Polymers via Sulfonation and Reductive Metallization;" Central Research; The Dow Chemical Company; pp. 267-294; 1990.

William J. Koros; "Barrier Polymers and Structures: Overview;" Department of Chemical Engineering; The University of Texas at Austin; pp. 1-21; Jan. 25, 1990.

(Continued)

*Primary Examiner*—Nicholas D Lucchesi
*Assistant Examiner*—Christopher D Koharski
(74) *Attorney, Agent, or Firm*—Squire, Sanders, Dempsey LLP.

(57) ABSTRACT

Materials having barrier characteristics are used with a balloon of a catheter assembly and a sheath for covering the balloon. The barrier materials prevent significant absorption of therapeutic substances used in association with the balloon, for example via a medicated prosthesis, into the balloon wall or the sheath. Accordingly the quantity and concentration of the therapeutic substances are preserved. Materials which can serve as a barrier include barrier polymers, polymers with additive fillers, polymers with a metallic coating, metallic films, polymers with a main group element oxide coating, and sulfonated or fluorinated polymers. For the sheath, materials such as glass and metals also function effectively.

2 Claims, 4 Drawing Sheets

OTHER PUBLICATIONS

"Classification of High-Barrier Polymers;" Barrier Polymers; vol. 3, pp. 487-492.

"VIII. Design Changes Based on Permeation and Leakage Studies;" pp. 39-46 and two (2) attached sheets.

Robert R. Reich; "Packaging Films: A Method of Microbial Barrier Evaluation;" Packaging Forum, MD&DI; pp. 19 and 21; Feb. 1986.

Sterling Anthony, Jr.; "Form, Fill, and Seal Paćkaging Machinery: An Overview;" Packaging Forum, MD&DI; pp. 18-22; Sep. 1985.

Sterling Anthony, Jr.; "The Retortable Pouch As a Medical Package;" Packaging Forum, MD&DI; pp. 18 and 20; Sep. 1984.

Carl D. Marotta; "Designing High-Barrier Plastics;" Packaging Forum, MD&DI pp. 26, 28, and attached page; Jun. 1986.

William Sacks; "Packaging Containers;" Chemtech; pp. 480-483; Aug. 1988.

Robert Colvin and Stephen Moore; "Range of Barrier Options Upgrade Flexible Packaging;" Modern Plastics; pp. 62-63; Oct. 1996.

* cited by examiner

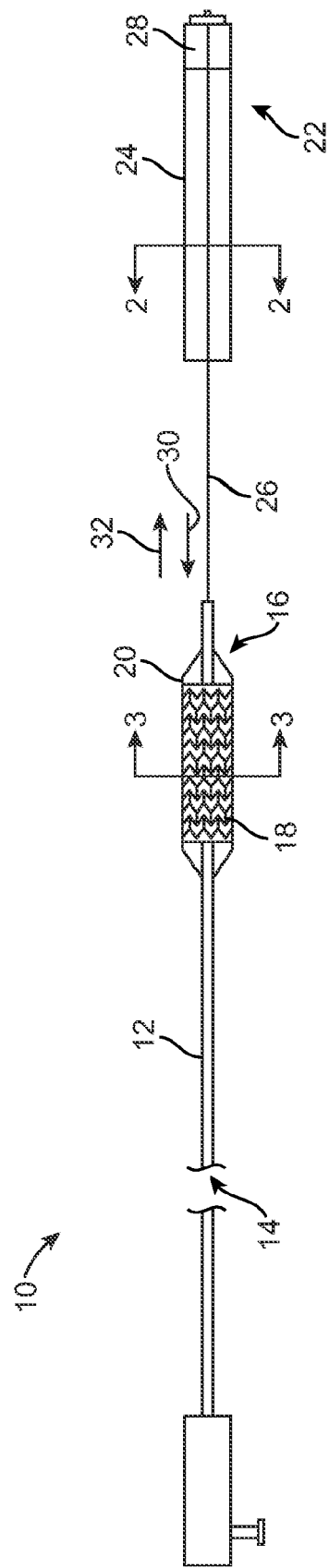
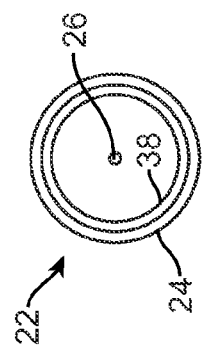

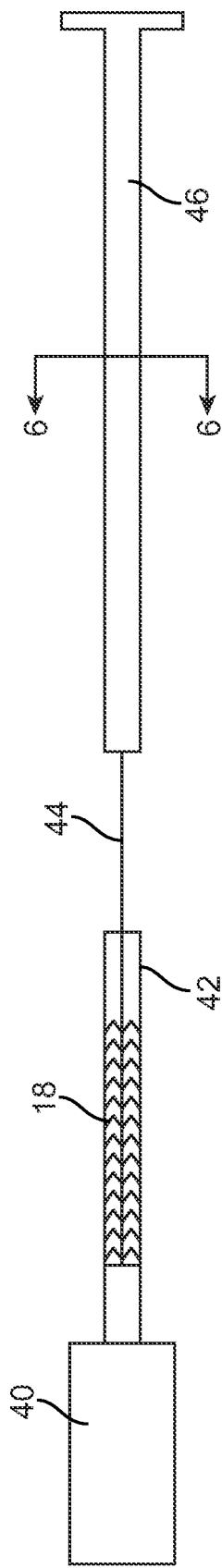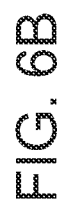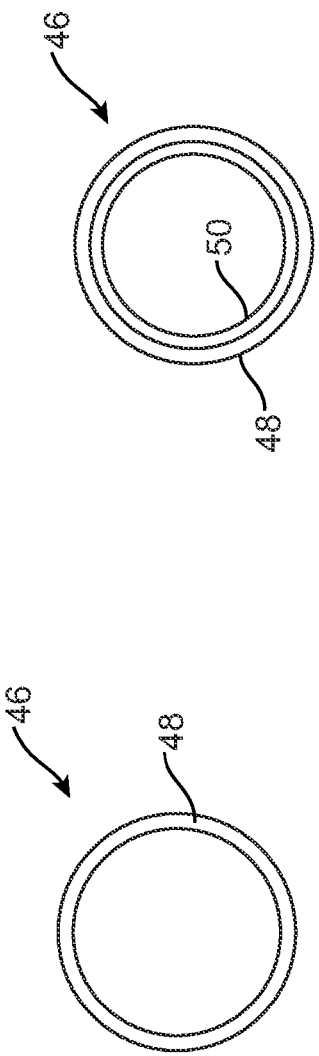
FIG. 5
FIG. 6B
FIG. 6A

DRUG DIFFUSION BARRIERS FOR A CATHETER ASSEMBLY

BACKGROUND OF THE INVENTION

1. Field of the Invention

The present invention relates to materials, such as polymers, having barrier characteristics generally desirable in medical devices. More specifically, the barrier materials described herein are particularly suitable for medical products such as balloons associated with catheters, and sheaths for protectively covering the balloons.

2. Description of the Related Art

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the arterial lumen. The balloon is then deflated to a smaller profile to allow the catheter to be withdrawn from the patient's vasculature.

In treating the damaged vasculature tissue and to deter thrombosis and restenosis, therapeutic substances are commonly administered to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively.

Systemic administration of such therapeutic substances in sufficient amounts to supply an efficacious concentration to the local treatment site often produces adverse or toxic side effects for the patient. Accordingly, local delivery is a preferred method of treatment since smaller total levels of medication are administered in comparison to systemic dosages, but the medication is concentrated at a specific treatment site. Local delivery thus produces fewer side effects and achieves more effective results.

A common technique for local delivery of therapeutic substances employs medicated stents. Stents that are capable of storing medication and releasing the medication at the implanted site are well known in the art. For example, a metallic stent is coated with a polymeric material which, in turn, is impregnated with a therapeutic substance or a combination of substances. Once the stent is implanted within a cardiovascular system lumen, the drug or drugs are released from the polymer for the treatment of the local tissues. U.S. Pat. No. 5,605,696 to Eury et al., U.S. Pat. No. 5,464,650 to Berg et al., and U.S. Pat. No. 5,700,286 to Tartaglia et al. are examples illustrating the use of a polymeric coating for the local delivery of a therapeutic substance or substances.

A problem associated with devices for carrying and delivering a therapeutic substance is diffusion of the substance from an element that carries the substance. Diffusion of the therapeutic substance from the carrying element potentially reduces the concentration and quantity of the substance below the level sufficient for effective treatment of the patient. In a catheter assembly, polymeric materials that contact the carrying element have a potential to significantly absorb the therapeutic substances. For example, drugs readily absorb into the wall layer of a balloon or a sheath of a catheter assembly that protects the balloon during packaging. Accordingly, it is desirable to prevent diffusion of drugs into other components of the catheter assembly, thereby preserving the concentration and quantity of the drugs carried by the catheter carrying element.

SUMMARY OF THE INVENTION

In accordance with various aspects of the present invention, a sheath having a sheath layer removably covers a device such as a balloon of a catheter assembly. The balloon is capable of carrying a therapeutic substance, for example, via an implantable device or prosthesis, one example of which includes a stent. In one embodiment, the sheath layer is formed from a barrier material that prevents the therapeutic substance from significantly diffusing from the device and absorbed absorbing into the sheath layer. In another embodiment, a barrier layer formed from the barrier material can be disposed on the inside surface of the sheath layer.

Another aspect of the present invention is a balloon associated with a catheter assembly. The balloon has a balloon wall made from a barrier material. The balloon is configured to be able to carry a therapeutic substance, for example, via an implantable prosthesis. The barrier material prevents the therapeutic substance from diffusing out of the prosthesis and being absorbed into the balloon wall. In accordance with another embodiment, a barrier layer made from the barrier material is disposed on the outer surface of the balloon wall.

For the sheath layer, the barrier material can be a barrier polymer, glass, or a metallic substance such as aluminum, stainless steel or gold. For the balloon, the barrier material can be made from a barrier polymer or a metallic film. The metallic film can be made from materials such as gold, platinum, platinum/iridium alloy, tantalum, palladium, chromium, and aluminum.

Suitable barrier polymers include polymers of polyolefins, polyurethanes, cellulosics, polyesters, polyamides, poly(hexamethylene isophthalamide/terephthalamide), poly(ethylene terephthalate-co-p-oxybenzoate), poly(hydroxy amide ethers), polyacrylates, polyacrylonitrile, acrylonitrile/styrene copolymer, rubber-modified acrylonitrile/acrylate copolymer, poly(methyl methacrylate), liquid crystal polymers, poly(phenylene sulfide), polystyrenes, polycarbonates, poly (vinyl alcohols), poly(ethylene-vinyl alcohol), epoxies composed of bisphenol A based diepoxides with amine cure, aliphatic polyketones, polysulfones, poly(ester-sulfone), poly(urethane-sulfone), poly(carbonate-sulfone), poly(3-hydroxyoxetane), poly(amino ethers), gelatin, amylose, parylene-C, parylene-D, parylene-N.

Representative polyolefins include polyolefins based upon alpha-monoolefin monomers having from about 2 to 6 carbon atoms and halogen substituted olefins. For example, low to high density polyethylenes, essentially unplasticized poly (vinyl chloride), poly (vinylidene chloride), poly (vinyl fluoride), poly (vinylidene fluoride), poly (tetrafluoroethylene), poly (chlorotrifluoroethylene), and mixtures thereof are suitable.

Representative polyurethanes include polyurethanes having a glass transition temperature above a storage or ambient temperature, or having a non-polar soft segment which includes a hydrocarbon, silicone, fluorosilicone, or mixtures thereof.

Representative examples of cellulosics include cellulose acetate having a degree of substitution (DS) greater than about 0.8 or less than about 0.6, ethyl cellulose, cellulose nitrate, cellulose acetate butyrate, methyl cellulose, and mixtures thereof.

Representative polyesters include saturated or unsaturated polyesters, including poly (butylene terephthalate), poly (ethylene terephthalate), and poly(ethylene 2,6-naphthalene dicarboxylate).

Representative polyamides include crystalline or amorphous polyamides including nylon-6, nylon-6,6, nylon-6,9, nylon-6,10, aromatic nylon MXD6, and mixtures thereof.

Representative polyacrylates include poly(methylmethacrylate) and polymethacrylate.

In accordance with another embodiment, platelet shaped inorganic fillers, such as mica, platelet silicas, flaked metal, flaked glass or the like may be combined with the aforementioned polymers.

In accordance with another embodiment, a sheath layer and a balloon wall can be made from a polymeric material having a metallic layer disposed on the therapeutic substance contacting surface of sheath layer and balloon wall. In an alternative embodiment, a layer of carbide or nitride compound such as titanium nitride, zirconium nitride, and silicon carbide function effectively.

In accordance with another embodiment, sheath layer and balloon wall can be made from a polymeric material having a main group element oxide layer, such as silicone oxide, or metal oxide layer formed on the therapeutic substance contacting surface of sheath layer and balloon wall.

In accordance with another embodiment, sheath layer 24 and balloon wall 20 can be made from a polymeric material, typically a barrier polymer, having the therapeutic substance contacting surface treated with sulfonation or fluorination to form a barrier layer.

BRIEF DESCRIPTION OF THE DRAWINGS

FIG. 1 is a partial view of a catheter assembly having a balloon disposed at the distal end of the catheter assembly and a sheath for removably covering the balloon;

FIG. 2A is a cross sectional view of one embodiment of the sheath shown in FIG. 1 taken in the direction of the arrow and along the plane of line 2-2 of FIG. 1;

FIG. 2B is a cross sectional view of one embodiment of the sheath shown in FIG. 1, taken in the direction of the arrow and along the plane of line 2-2 of FIG. 1;

FIG. 5 is an example of a packaging assembly used to transport a stent, the packaging includes a sheath;

FIG. 6A is a cross sectional view of one embodiment of the sheath shown in FIG. 5, taken in the direction of the arrow and along the plane of line 6-6 in FIG. 5; and FIG. 6B is a cross sectional view of one embodiment of the sheath shown in FIG. 5, taken in the direction of the arrow and along the plane of line 6-6 in FIG. 5.

DETAIL DESCRIPTION OF THE PREFERRED EMBODIMENTS

Figure 3B:
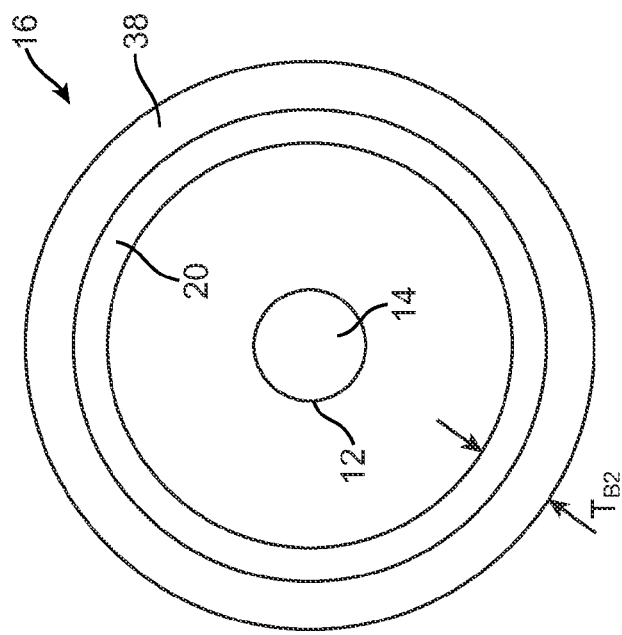
FIG. 3B is a cross sectional view of one embodiment of the balloon shown in FIG. 1, excluding a stent, taken in the direction of the arrow and along the plane of line 3-3 in FIG. 1.

The following definitions apply hereinthroughout unless a contrary intention is expressly indicated:

"Polymer," "poly," and "polymeric" means mean the product of a polymerization reaction and is are inclusive of homopolymers, copolymers, terpolymers etc., including random, alternating, block, and graft variations thereof.

"Oxygen transmission rate" means permeation rate of oxygen in cm$^3$ per mil (0.001 inch, 0.0254 mm) of material (e.g., a polymer) per 100 in$^2$ (645 cm$^2$) of surface per day (24 hrs.) at 1 atm (760 mm Hg), 73° F. (23° C.), and 75% relative humidity.

"Water transmission rate" means permeation rate of water vapor in grams per mil (0.001 inch, 0.0254 mm) of material (e.g., a polymer) per 100 in$^2$ (645 cm$^2$) of surface per day (24 hrs.) at 1 atm (760 mm Hg), 100° F. (38° C.), and 90% relative humidity.

Referring now to the drawings, wherein similar parts are identified by like reference numerals, FIG. 1 is a partial view of a catheter assembly 10, that is well known by one of ordinary skill and in the art and used in a variety of medical procedures such as percutaneous transluminal coronary angioplasty (PTCA), vascular prosthetic implantation, and atherectomy. The type of catheter assembly 10 is not of critical importance. Catheter assembly 10 includes catheter tube 12 having a guidewire lumen 14. Guidewire lumen 14 is configured to receive a guidewire (not shown) which is used to maneuver catheter tube 12 through the vasculature of a subject.

A balloon assembly 16, incorporated at the distal end of catheter tube 12, is adapted for carrying an expandable prosthesis 18, an example of which includes a stent. The particular type and structure of stent 18 is not critical so long as stent 18 is capable of securing a therapeutic substance and releasing the substance in vivo. The methods of loading therapeutic substances onto stent 18 are well known and practiced by one of ordinary skill in the art. Balloon 16 is defined by a balloon wall 20 which is inflatable to dilate from a collapsed configuration to an expanded configuration. Balloon wall 20 is deflatable after inflation to selectively return to the collapse configuration. As illustrated in FIG. 3A, balloon wall 20 can have any suitable thickness $T_{B1}$ so long as thickness $T_{B1}$ does not compromise properties that are critical for achieving optimum performance. The properties include high burst strength, low compliance, good flexibility, high resistance to fatigue, the ability to fold, the ability to cross and recross an occluded region or a desired region of treatment, and low susceptibility to defect caused by handling. By way of example, and not limitation, thickness $T_{B1}$ can be in a range from about 5 microns to about 75 microns, the specific measurement depending on the procedure for which balloon 16 is to be used.

As illustrated in FIGS. 1 and 2A, a sheath 22 is provided for protecting balloon 16, with or without stent 18, by covering balloon 16 during transportation of a packaged catheter assembly 10. Sheath 22 is defined by a sheath layer 24 forming a generally hollow, tubular body. As illustrated in FIG. 2A, sheath layer 24 can have any suitable thickness $T_S$. A guidewire 26 is secured to a closed end 28 of sheath 22. Sheath 22 encapsulates balloon 16, with or without stent 18, by inserting guidewire 26 into guidewire lumen 14 of catheter assembly 10 and thrusting sheath 22 in the direction of arrow 30. Sheath 22 can be removed from balloon 16 prior to treating a subject by reversing the process and withdrawing sheath 22 in the direction of arrow 32 until guidewire 26 is completely removed from guidewire lumen 14.

Figure 4:
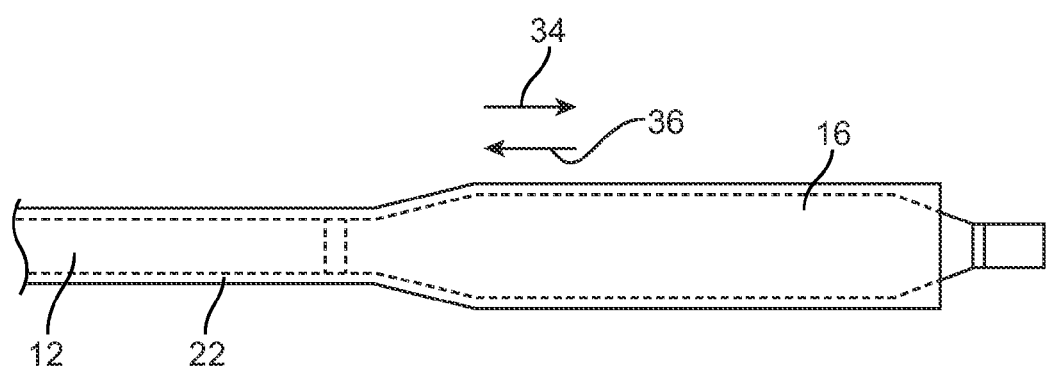
FIG. 4 is a partial view of a catheter assembly having a balloon disposed on the distal end of the catheter assembly and a sheath for removably covering the balloon.

Sheath 22 is not limited to the above-described structure and other variations of sheath 22 for covering balloon 16 are equally applicable. For example, in another embodiment as illustrated in FIG. 4, sheath 22 is structurally generally defined by an elongated hollow sleeve, circumscribing at least a portion of catheter tube 12. Sheath 22 allows a user to cover balloon 16, with or without stent 18, by moving sheath 22 in the direction of arrow 34. Prior to inserting balloon 16 into the vasculature system of a subject or subsequent to insertion but prior to inflating balloon 16, sheath 22 can be removed by withdrawing the elongated tube in the direction of arrow 36.

In one embodiment, balloon wall 20 and sheath layer 24 are formed from a barrier material. The barrier material prevents significant diffusion of therapeutic substances out from stent 18 and prevents significant absorption of the substances into sheath layer 24 and balloon wall 20.

Figure 3A:
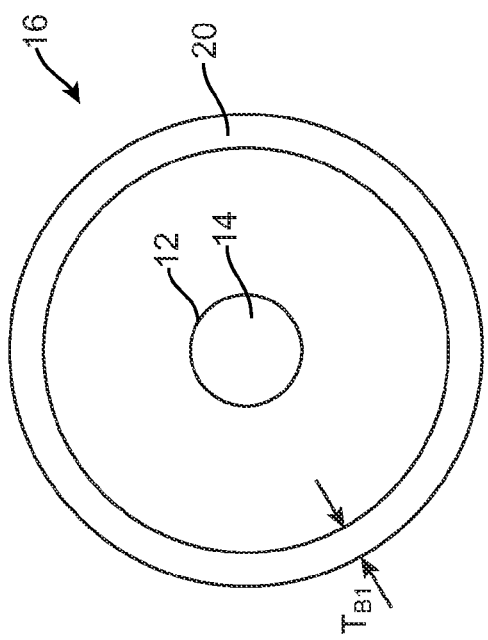
FIG. 3A is a cross sectional view of one embodiment of the balloon shown in FIG. 1, excluding a stent, taken in the direction of the arrow and along the plane of line 3-3 of FIG. 1.

In an alternative embodiment, as illustrated in FIGS. 2B and 3B, a barrier layer 38 formed from the barrier material may be formed on the inside surface of sheath layer 24, such as the therapeutic substance-contacting surface, or on the outside surface of balloon wall 20, such as the therapeutic substance-contacting surface. The underlying sheath layer 24 and balloon wall 20 can be made from any suitable material. For sheath 22, barrier layer 38 has any suitable thickness. For balloon 16, the total thickness $T_{B2}$ of balloon wall 20 and barrier layer 38 is any thickness that does not compromise desirable properties of the balloon. As indicated above, total thickness $T_{B2}$ should not hinder optimum performance characteristics including high burst strength, low compliance, good flexibility, high resistance to fatigue, folding ability, the ability to cross and recross the desired site of treatment, and low susceptibility to defect caused by handling. By way of example, and not limitation, barrier layer 38 can have a thickness of about 0.1 to about 25 microns with the underlying balloon wall 20 having a thickness of about 5 to 75 microns. A specific choice of thickness $T_{B2}$ depends on the anatomy and size of the target vessel in which balloon 16 is inserted. The structures of FIGS. 2B and 3B can be manufactured, for example, by lamination, co-extrusion, or coating. Lamination is the process of adhesively bonding two or more materials. Co-extrusion is the process of extruding two or more materials through a single die with two or more orifices arranged so that the extrudants merge and weld together into a laminar structure. The laminar structure, for example is then chilled such as by quenching. Coating is a process in which a liquid is applied continuously to a moving sheet to produce a uniform application of the fluid onto and/or within the sheet. The processes of lamination, co-extrusion, and coating are well known to one of ordinary skill in the art.

In another embodiment, balloon wall 20, sheath layer 24, and barrier layer 38 may include a plurality of layers, each layer being formed from the same material, a different material, or a mixture of barrier materials.

Typically, the barrier material should have an oxygen transmission rate of not more than about 200 cc/100 in$^2$, usefully not more than about 100 cc/100 in$^2$ for 1 mil per 24 hrs. at 73° F., 75% relative humidity, and 1 atm. A suitable barrier material should have a water vapor transmission rate of not more than 20 gm/100 in$^2$ for 1 mil per 24 hrs. at 100° F., 90% relative humidity, and 1 atm.

For the sheath layer 24, the barrier material can be a barrier polymer, glass or a metallic substance such as aluminum, stainless steel or gold. For the balloon 16, the barrier material can be a barrier polymer or a metallic film. Suitable examples of films include, but not limited to, gold, platinum, platinum/iridium alloy, tantalum, palladium, chromium, and aluminum.

Suitable barrier polymers include polymers of polyolefins, polyurethanes, cellulosics (i.e., polymers having mer units derived from cellulose), polyesters, polyamides, poly(hexamethylene isophthalamide/terephthalamide) (commercially available as Selar PA™), poly(ethylene terephthalate-co-p-oxybenzoate) (PET/PHB, e.g., copolymer having about 60-80 mole percent PHB), poly(hydroxy amide ethers), polyacrylates, polyacrylonitrile, acrylonitrile/styrene copolymer (commercially available as Lopac™), rubber-modified acrylonitrile/acrylate copolymer (commercially available as Barex™), poly(methyl methacrylate), liquid crystal polymers (LCP) (e.g., Vectra™ available from Hoescht-Celanese, Zenite™ available from DuPont, and Xydar™ available from Amoco Performance Chemicals), poly(phenylene sulfide), polystyrenes, polycarbonates, poly(vinyl alcohols), poly(ethylene-vinyl alcohol) (EVAL, e.g., having about 27 to about 47 mole percent of ethylene content), epoxies composed of bisphenol A based diepoxides with amine cure, aliphatic polyketones (e.g., Carilon™ available from Shell, and Ketonex™ available from British Petroleum), polysulfones, poly(ester-sulfone), poly(urethane-sulfone), poly(carbonate-sulfone), poly(3-hydroxyoxetane), poly(amino ethers), gelatin, amylose, parylene-C, parylene-D, parylene-N.

Representatives polyolefins include those based upon alpha-monoolefin monomers having from about 2 to 6 carbon atoms and halogen substituted olefins, i.e., halogenated polyolefins. By way of example, and not limitation, low to high density polyethylenes, essentially unplasticized poly (vinyl chloride), poly (vinylidene chloride), poly (vinyl fluoride), poly (vinylidene fluoride), poly (tetrafluoroethylene) (Teflon), poly (chlorotrifluoroethylene) (Kel-F™), and mixtures thereof are suitable. Low to high density polyethylenes are generally understood to have densities of about 0.92 g cm$^{-3}$ to about 0.96 g cm$^{-3}$, however, no bright line can be drawn for density classifications and the density can vary according to the supplier.

Representative polyurethanes include polyurethanes having a glass transition temperature above a storage or ambient temperature, for example having a glass transition temperature of at least 40° C. to 60° C., or having a non-polar soft segment which includes a hydrocarbon, silicone, fluorosilicone, or mixtures thereof. For example, Elast-Eon™, manufactured by Elastomedic/CSIRO Molecular Science, is a polyurethane with a non-polar soft segment which is made from 1,4-butanediol, 4,4'-methylenediphenyl diisocyanate, and a soft segment composed of a blend poly(hexamethylene oxide) (PHMO) and bishydroxyethoxypropylpolydimethylsiloxane (PDMS). A useful example has a blend of 20% by weight PHMO and 80% by weight PDMS.

Representative examples of cellulosics include, but are not limited to, cellulose acetate having a degree of substitution (DS) greater than about 0.8 or less than about 0.6, ethyl cellulose, cellulose nitrate, cellulose acetate butyrate, methyl cellulose, and mixtures thereof.

Representative polyesters include saturated or unsaturated polyesters such as, but no limitation to, poly (butylene terephthalate), poly(ethylene 2,6-naphthalene dicarboxylate) (PEN), and poly (ethylene terephthalate).

Representative polyamides include crystalline or amorphous polyamides such as, but not limited to, nylon-6, nylon-6,6, nylon-6,9, nylon-6,10, aromatic nylon MXD6 (manufactured by Mitsubishi Gas Chemical America Inc.), and mixtures thereof.

Representative polyacrylates include, but are not limited to, poly(methylmethacrylate) and polymethacrylate.

In one embodiment, the barrier polymer can be a mixture of the aforementioned polymers. For example, a barrier layer can comprise about 70% to about 99% by weight acrylonitrile and about 30% to about 1% by weight styrene. Similarly, copolymers of vinyl chloride and vinylidene chloride with a vinyl chloride content of about 1 to about 30 mole percent and PET/PHB copolymers with a PHB content of about 60 to about 80 mole percent function effectively.

Table I illustrates the oxygen and water transmission rate of some of the aforementioned polymers:

TABLE I

| Polymer | Transmission Rate | |
|---|---|---|
| | Oxygen[1] | Water[2] |
| low density polyethylene | 300 | 1.4 |
| high density polyethylene | 110 | 0.38 |
| polypropylene | 150 | 0.66 |
| nylon-12 | — | 63.5 |
| polystyrene | 300 | 7 |
| polycarbonate | 200 | 11.4 |
| nylon-6/nylon-6,6 | 2.6 | 8 |
| nylon-11 | — | 3.8 |
| polyacrylonitrile | 0.8 | 4 |
| poly (vinyl chloride) | 10 | 2.2 |
| poly(acrylonitrile-co-styrene)(Barex ™) | 1.0 | 6.1 |
| poly(ethylene terephthalate) | 3.0-11 | 1.8 |
| poly (ethylene 2,6-naphthalene dicarboxylate (PEN) | 1.3 | — |
| aromatic nylon MDX6 | 0.2 | — |
| poly (vinylidene chloride) | 0.07 | 0.08-0.2 |
| EVAL | 0.02 | 1.5-3.8 |

[1]Permeation rate of oxygen in cm$^3$ per mil (0.001 inch, 0.0254 mm) of material (e.g., a polymer) per 100 in$^2$ (645 cm$^2$) of surface per day (24 hrs.) at 1 atm (760 mm Hg), 73° F. (23° C.), and 75% relative humidity.
[2]Permeation rate of water vapor in grams per mil (0.001 inch, 0.0254 mm) of material (e.g., a polymer) per 100 in$^2$ (645 cm$^2$) of surface per day (24 hrs.) at 1 atm (760 mm Hg), 100° F. (38° C.), and 90% relative humidity.

The choice of the most effective barrier polymer depends on the selection of the particular therapeutic substance. Factors for selecting an appropriate polymer include molecular structure and solubility of the polymer and therapeutic substance, the crystallinity or amorphousness of the polymer, and the size or molecular weight of the therapeutic substance. In general, and not strictly bound by this broad proposition, polymers that are similar in structure to the therapeutic substance are poor barriers, and therapeutic substances that have an equivalent solubility parameter to the polymer's solubility parameter diffuse more readily into the polymer. The solubility parameter is defined as the square root of the term "the energy of evaporation of the material to a gas at zero pressure per cubic centimeter of material," Polymer Handbook, Brandrup & Immergut, Wiley Interscience, 1975. Polymers having high crystallinity and therapeutic substances having large molecules are suitable combinations.

Examples of therapeutic substances or agents typically used to treat a subject include, antineoplastic, antiinflammatory, antiplatelet, anticoagulants, fribrinolytic, thrombin inhibitor, antimitotic, and antiproliferative substances. Examples of antineoplastics include paclitaxel and docetaxel. Examples of antiplatelets, anticoagulants, fribrinolytics, and thrombin inhibitors include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycine. Examples of cytostatic or antiproliferative agents include rapamycin, angiopeptin (a somatostatin analogue from Ibsen), angiotensin converting enzyme inhibitors such as Captopril® (available from Squibb), Cilazapril® (available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, prostaglandins such as PGE-1, and dexamethasone. While the foregoing therapeutic substances or agents are well known for their preventative and treatment purposes, the substances or agents are provided by way of example and are not meant to be limiting. Other therapeutic substances which are currently available or that may be developed in the future are equally applicable for use with the present invention. The treatment of patients using the above mentioned medicines is well known to those having ordinary skill in the art.

Table II is an exemplary list of some of the aforementioned barrier polymers and the therapeutic substances that can be used with the barrier polymers. It is understood that may other suitable combinations are possible.

TABLE II

| Barrier Polymer | Therapeutic Substance |
|---|---|
| poly (ethylene terephthalate) | paclitaxel |
| poly (vinylidene chloride) | paclitaxel |
| Nylon-6 | dexamethasone |
| polyacrylonitrile | dexamethasone |
| poly (tetrafluoroethylene) | 5-Fluorouracil |
| poly (vinyl chloride) | 5-Fluorouracil |
| poly (ethylene terephthalate) | PGE-1 |
| polyacrylonitrile | PGE-1 |
| EVAL (poly ethylene-co-vinyl alcohol; 32 mol % ethylene) | Probucol |
| Nylon-6 | Probucol |
| Poly(vinylidene chloride) | Colchicine |
| Liquid crystal polymers | Argatroban |
| Polyacrylonitrile | Rapamycin |
| Nylon-6 | Rapamycin |
| EVAL | Rapamycin |
| Poly(vinyl chloride)-unplasticized | Etoposide phosphate |
| Poly (ethylene 2,6-naphthalene dicarboxylate) (PEN) | Camptothecin |

In accordance with another embodiment, platelet shaped inorganic fillers, such as mica, platelet silicas, flaked metal, flaked glass or the like, may be used to improve the barrier properties of the aforementioned polymers. Filler technology is known to one of ordinary skill in the art. Examples in the patent literature on the use of such fillers include U.S. Pat. No. 3,463,350 (disclosing use of mica in polyethylene), British Patent No. 1,136,350 (disclosing use of platelet type fillers in a variety of polymers including polyethylene and polystyrene), U.S. Pat. No. 4,983,432 (disclosing blend of mica particles in ethylene-vinyl alcohol), and U.S. Pat. Nos. 4,528, 235 and 4,618,528 (disclosing thin polymer films containing small sized platelet type fillers). The weight ratio of fillers with respect to the polymer depends on the type of filler and polymer or polymer mixture and the improvement in barrier property that is desired. The calculation of the weight ratio of the blended composition is well known to one of ordinary skill in the art.

In accordance with another embodiment, sheath layer 24 and/or balloon wall 20 can be made from a polymeric material having a metallic layer disposed on the therapeutic substance contacting surface of sheath layer 24 and/or balloon wall 20.

Examples of metallic substances include, but are not limited to, aluminum, platinum, and gold. The metallic layer can be formed by physical vapor deposition, such as evaporation or sputtering, electrode-less plating, electroplating, or plasma assisted chemical vapor deposition. The methods of physical and chemical vapor deposition, electrode-less plating, and electroplating are well known and understood by one of ordinary skill in the art. In an alternative embodiment, a layer of carbide or nitride compound such as titanium nitride, zirconium nitride, and silicon carbide function effectively.

In accordance with another embodiment, sheath layer 24 and/or balloon wall 20 can be made from a polymeric material having a main group element oxide layer such as silicon oxide or metal oxide layer formed on the therapeutic substance contacting surface of sheath layer 24 and/or balloon wall 20. Examples of metal oxide coating include aluminum, chromium, and titanium oxide. Formation of a main group element oxide is known by one of ordinary skill in the art.

In accordance with another embodiment, sheath layer 24 and/or balloon wall 20 can be made from a polymeric material, typically a barrier polymer, having the therapeutic substance contacting surface treated with sulfonation or fluorination to form a barrier layer. As is well known by one of ordinary skill in the art, sulfonation is achieved by exposure of the polymer to sulfur trioxide ($SO_3$). Processing parameters such as the time of exposure, concentration of sulfur trioxide, and temperature vary with the selected type of polymer, the selected polymer's crystallinity, and the particular therapeutic substance being considered. A fluorinated polymer can be produced, for example, by the AIROPAK process using nitrogen-diluted fluorine as the inflation gas, as described by U.S. Pat. No. 3,862,284 to Dixon.

EXAMPLES

Various suitable combinations of barrier material and therapeutic substances, including examples of useful thickness, are illustrated by the following set forth examples which are being given by way of illustration only and not by way of limitation.

Example 1

Sheath layer 24 is made from a barrier material comprising about 100% by weight poly(ethylene terephthalate). Sheath layer 24 has $T_S$ thickness of about 250 microns. Sheath 22 can be used with paclitaxel or PGE-1.

Example 2

Sheath layer 24 is made from a barrier material comprising borosilicate glass. Sheath layer 24 has a thickness of about 50 microns. Sheath 22 can be used with paclitaxel or PGE-1.

Example 3

Balloon wall 20 is made from a barrier material comprising about 30 mole percent vinyl chloride and 70 mole percent vinylidene chloride. Balloon wall 20 has thickness $T_{B1}$ of about 20 microns. Balloon wall 20 can be used with stent 18 carrying colchicine or 5-fluorouracil.

Example 4

Balloon 16 has barrier layer 38 disposed on balloon wall 20. Balloon wall 20 is made from about 100% by weight polyurethane composed of methylene diphenyl diisocyanate, polytetramethylene glycol and butanediol. Barrier layer 38 is about 100% by weight non-polar polyurethane composed of 1,4-butanediol, 4,4'-methylenediphenyl diisocyanate, and a soft segment composed of 20% by weight (PHMO) and 80% by weight (PDMS). Balloon wall 20 has thickness $T_{B1}$ of about 20 microns and barrier layer 38 has a thickness of about 10 microns. Balloon 16 can be used with a polymeric carrier impregnated with 5-fluorouracil, etoposide phosphate, hirudin, or heparin.

Example 5

Balloon 16 has barrier layer 38 disposed on balloon wall 20. Balloon wall 20 is made from about 100% by weight nylon-12. Barrier layer 38 is made from about 100% by weight nylon-6. Balloon wall 20 has thickness $T_{B1}$ of about 10 microns. Barrier 38 has a thickness of about 4 microns. Balloon can be used with rapamycin.

Example 6

Balloon 16 has barrier layer 38 disposed on balloon wall 20. Balloon wall 20 is made from about 100% by weight nylon-6. Barrier layer 38 is made from about 100% by weight EVOH (ethylene mole percent 44%). Balloon wall 20 has thickness $T_{B1}$ of about 10 microns. Barrier layer 38 has a thickness of about 10 microns. Balloon 16 can be used with stent 18 having a polymeric carrier impregnated with colchicine.

Example 7

Balloon 16 comprises barrier layer 38 disposed on balloon wall 20. Balloon wall 20 is made from about 100% by weight PEBAX 70D™ (manufactured by Elf Atochem). Barrier layer 38 is made from about 100% by weight nylon-6. Balloon wall 20 has thickness $T_{B1}$ of about 10 microns. Barrier layer 38 has a thickness of about 4 microns. Barrier layer 38 prevents any significant diffusion of agatroban into balloon wall 20.

Example 8

Balloon 16 comprises barrier layer 38 disposed on balloon wall 20. Balloon wall 20 is made from about 100% by weight Pellethane 70D™ (manufactured by Dow Chemicals). Barrier layer 38 is made from about 100% by weight poly (vinylidene chloride). An adhesive tie of Plexar™ (available from Quantum Chemicals or Equistar Chemicals) is disposed between balloon wall 20 and barrier layer 38. Balloon wall 20 has thickness $T_{B1}$ of about 10 microns. Barrier layer 38 has a thickness of about 10 microns. Barrier layer 38 prevent any significant diffusion of toposide sulfate into balloon wall 20.

Example 9

Balloon 16 has barrier layer 38 disposed on balloon wall 20. Balloon wall 20 is made from about 100% by weight nylon-12. Barrier layer 38 is made from about 100% by weight poly (ethylene terephthalate). Balloon wall 20 has thickness $T_{B1}$ of about 8 microns. Barrier layer 38 has a thickness of about 4 microns. Balloon 16 can be used with stent 18 having a polymeric coating impregnated with 5-fluorouracil.

Example 10

Balloon wall 20 is made from about 100% by weight nylon-12. A layer of gold is deposited by PVD to form a coating on balloon wall 20. Balloon wall 20 has thickness $T_{B1}$ of about 12 microns. The gold layer has a thickness of about 0.5 microns. Balloon 16 can be used with a polymeric carrier impregnated with dexamethasone.

Example 11

Balloon wall 20 is made from about 100% by weight Pebax 70D™. A layer of platinum is deposited by PVD to form a coating on balloon wall 20. Balloon wall 20 has thickness $T_{B1}$ of about 12 microns. The platinum layer has a thickness of about 0.5 microns. The platinum layer prevents omega 3-fatty acids from diffusing into the balloon wall 20.

Example 12

Balloon 16 has barrier layer 38 disposed on balloon wall 20. Balloon wall 20 is made from about 100% by weight poly(ethylene terephthalate). Barrier layer 38 is made from about 100% by weight liquid crystal polymer. An adhesive tie layer is disposed between balloon wall 20 and barrier layer 38. Balloon wall 20 has thickness $T_{B1}$ of about 10 microns. Barrier layer 38 has a thickness of about 4 microns. Balloon 16 can be used with tranilast.

Example 13

Balloon wall 20 is made from high density polyethylene. The outer surface of balloon wall 20 is sulfonated by sulfur trioxide to form a barrier layer. Balloon wall 20 has thickness $T_{B1}$ of about 20 microns. The barrier layer is now part of balloon wall 20 and has a thickness of about 10 microns. The barrier layer prevents any significant diffusion of PGE-1 into balloon wall 20.

Example 14

Balloon wall 20 is made from high density polyethylene. The outer surface of balloon wall 20 is fluorinated using fluorine blended with nitrogen (or alternatively argon). Balloon wall 20 has thickness $T_{B1}$ of about 20 microns. The barrier layer is now part of the balloon wall 20 and has a thickness of about 10 microns. The barrier layer prevents any significant diffusion of dexamethasone into balloon wall 20.

In an illustrative commercial kit, catheter assembly 10 having sheath 22, removably encapsulating balloon 16, is sterilized and packaged for usage by a user, such as a physician. A user can simply remove catheter assembly 10 having sheath 22 from the sterile commercial kit prior to the implantation procedure. It one embodiment of the commercial kit, catheter assembly 10 may be provided having stent 18 crimped on balloon 16. Alternatively, stent 18 may be provided in a separate commercial kit, sterilized and packaged. A user has to remove stent from the separate commercial kit and crimp stent 18 onto balloon 16. An example of a commercial kit containing stent 18 is illustrated in FIG. 5. A sleeve or sheath 42 extends from a base 40 and supports stent 18. A guidewire 44 extends through sleeve 42. To mount stent 18 on balloon 16, guidewire 44 is inserted in guidewire lumen 14 of catheter assembly 10, wherein balloon 16 partially penetrates into sleeve 42. Stent 18 is slid onto balloon 16 and crimped thereon. Sheath 46, the particular structure of which is not of critical importance, encapsulates stent 18 and protects stent 18 during transportation. Sheath 46 can be generally similar in structure to aforementioned sheath 22 of FIG. 1, absent guidewire 26. As illustrated in FIG. 6A sheath 46 is also defined by a layer 48 formed from a barrier material to prevent therapeutic substance(s) from diffusing out of stent 18 and absorbing into layer 48. Sheath 46, as illustrated in FIG. 6B may comprise at least one barrier layer 50 disposed on the inner surface of layer 48. It is also understood that sleeve 42 may be formed from a barrier material.

While the particular embodiments of the present invention have been shown and described, it will be obvious to those skilled in the art that changes and modifications can be made without departing from this invention in its broader aspects. For example, a sheath may be provided, having an inner surface that does not contact a balloon and/or stent. Accordingly, therapeutic substances do not absorb or diffuse into the sheath material. Therefore, the appended claims are to encompass within their scope all such changes and modifications as fall within the true spirit and scope of this invention.

What is claimed is:

1. A sheath comprising a hollow body, the sheath being adapted to removably cover at least part of an implantable medical device that carries a therapeutic substance, wherein the sheath material prevents the therapeutic substance from significantly absorbing into the sheath, wherein the sheath material has an oxygen transmission rate of not more than 200 cc/100 in$^2$ for 1 mil per 24 hours at 73° F., 75% relative humidity and 1 atmosphere, and wherein the sheath material has a water vapor transmission rate of not more than 20 gm/100 in$^2$ for 1 mil per 24 hrs. 100° F. 90% relative humidity and 1 atm, wherein the implantable object is a balloon integrated with a catheter, wherein the balloon material, sheath material, or both comprise the same or different polymeric material, wherein the polymeric material comprises a polyurethane having a glass transition temperature above a storage temperature.

2. A sheath comprising a hollow body, the sheath being adapted to removably cover at least part of an implantable medical device that carries a therapeutic substance, wherein the sheath material prevents the therapeutic substance from significantly absorbing into the sheath, wherein the sheath material has an oxygen transmission rate of not more than 200 cc/100 in$^2$ for 1 mil per 24 hours at 73° F., 75% relative humidity and 1 atmosphere, and wherein the sheath material has a water vapor transmission rate of not more than 20 gm/100 in$^2$ for 1 mil per 24 hrs. 100° F. 90% relative humidity and 1 atm, wherein the implantable object is a balloon integrated with a catheter, wherein the balloon material, sheath material, or both comprise the same or different polymeric material, wherein the polymeric material comprises a polyurethane having a non-polar soft segment wherein the non-polar soft segment is selected from hydrocarbons, silicones, fluorosilicones, or their mixtures.

* * * * *